US011931506B2

(12) United States Patent
Li et al.

(10) Patent No.: US 11,931,506 B2
(45) Date of Patent: Mar. 19, 2024

(54) DRY POWDER INHALER

(71) Applicant: Chia Tai Tianqing Pharmaceutical Group Co., Ltd., Lianyungang (CN)

(72) Inventors: Changhui Li, Lianyungang (CN); Ping Dong, Lianyungang (CN); Xuebing Zhu, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 629 days.

(21) Appl. No.: 16/766,646

(22) PCT Filed: Nov. 22, 2018

(86) PCT No.: PCT/CN2018/116942

§ 371 (c)(1),
(2) Date: May 22, 2020

(87) PCT Pub. No.: WO2019/101135

PCT Pub. Date: May 31, 2019

(65) Prior Publication Data

US 2020/0360631 A1 Nov. 19, 2020

(30) Foreign Application Priority Data

Nov. 23, 2017 (CN) ........................ 201711177647.1

(51) Int. Cl.
*A61M 15/00* (2006.01)

(52) U.S. Cl.
CPC .... *A61M 15/0035* (2014.02); *A61M 15/0008* (2014.02); *A61M 15/0051* (2014.02)

(58) Field of Classification Search
CPC ..... A61M 15/00–0008; A61M 15/0028–0041; A61M 15/0045–0051;

(Continued)

(56) References Cited

U.S. PATENT DOCUMENTS 4,423,724 A * 1/1984 Young ............... A61M 15/0028 128/203.15
4,889,114 A 12/1989 Kladders (Continued)

FOREIGN PATENT DOCUMENTS

CA 2972826 A1 7/2016
CN 1646095 A 7/2005

(Continued)

OTHER PUBLICATIONS

Notification of Transmittal, the International Search Report, and the Written Opinion of the International Searching Authority for PCT/CN2018/116943; dated Feb. 26, 2019.

(Continued)

*Primary Examiner* — Rachel T Sippel
*Assistant Examiner* — Jacqueline M Pinderski
(74) *Attorney, Agent, or Firm* — TOPE-MCKAY & ASSOCIATES

(57) ABSTRACT

A novel dry powder inhaler. By providing a plurality of capsule chambers (1*a*, 1*b*, 1*c*, 1*d*) arranged in parallel in a capsule dry powder inhalation device, a medicine dispenser containing active components of a composite product or their mixture separately is provided. The dry powder inhaler has a simple structure and is convenient to operate. In addition, the parameters of air inlet channels and an air outlet channel can be adjusted by means of each capsule chamber (1*a*, 1*b*, 1*c*, 1*d*) according to the properties of powder of a medicine or a combination, so as to provide an appropriate particle distribution for each active component.

16 Claims, 14 Drawing Sheets

(58) Field of Classification Search
CPC ........ A61M 11/00–003; A61M 11/006; A61M 11/008; A61M 15/002–0026; A61M 2206/20; A61M 2202/064; A61M 2206/12; A61M 2206/16
See application file for complete search history.

(56) References Cited

U.S. PATENT DOCUMENTS

| | | | | |
|---|---|---|---|---|
| 5,002,048 | A | 3/1991 | Makiej, Jr. | |
| 5,901,883 | A | 5/1999 | Ritsche | |
| 5,947,118 | A | 9/1999 | Hochrainer et al. | |
| 6,073,629 | A * | 6/2000 | Hardy | A61M 11/002 128/203.15 |
| 6,119,688 | A * | 9/2000 | Whaley | A61M 15/0091 128/203.15 |
| 6,230,707 | B1 * | 5/2001 | Horlin | A61M 11/002 128/203.15 |
| 8,196,578 | B2 | 6/2012 | Wendland | |
| 8,978,645 | B2 * | 3/2015 | Chen | A61M 15/0015 128/203.23 |
| 2003/0235538 | A1 * | 12/2003 | Zierenberg | A61M 15/0021 128/200.23 |
| 2004/0206350 | A1 | 10/2004 | Alston et al. | |
| 2006/0207596 | A1 * | 9/2006 | Lane | A61M 15/08 128/207.18 |
| 2007/0181124 | A1 | 8/2007 | Casper et al. | |
| 2007/0295332 | A1 * | 12/2007 | Ziegler | A61M 15/0028 128/203.15 |
| 2008/0289629 | A1 * | 11/2008 | Djupesland | A61M 15/002 128/203.15 |
| 2009/0165791 | A1 | 7/2009 | Wendland | |
| 2009/0178676 | A1 | 7/2009 | Villax et al. | |
| 2010/0000528 | A1 * | 1/2010 | Palmer | A61M 15/0045 128/203.15 |
| 2012/0145150 | A1 * | 6/2012 | Donovan | A61M 15/001 128/203.15 |
| 2013/0255679 | A1 | 10/2013 | Andrade et al. | |
| 2013/0340747 | A1 * | 12/2013 | Donovan | A61M 15/0086 128/200.23 |
| 2015/0059747 | A1 * | 3/2015 | Von Schuckmann | A61M 15/0035 128/203.15 |
| 2016/0022931 | A1 * | 1/2016 | Althorpe | A61M 11/003 128/203.12 |
| 2016/0199598 | A1 | 7/2016 | Curtis et al. | |

FOREIGN PATENT DOCUMENTS

| | | | |
|---|---|---|---|
| CN | 1953779 | A | 4/2007 |
| CN | 101380496 | A | 3/2009 |
| CN | 101443066 | A | 5/2009 |
| CN | 101574552 | A | 11/2009 |
| CN | 103237570 | A | 8/2013 |
| CN | 204501970 | U | 7/2015 |
| CN | 105107070 | A | 12/2015 |
| CN | 204951865 | U | 1/2016 |
| CN | 105920709 | A | 9/2016 |
| CN | 106031810 | A | 10/2016 |
| CN | 106913943 | A | 7/2017 |
| CN | 106924845 | A | 7/2017 |
| CN | 208389129 | U | 1/2019 |
| JP | 1998234827 | A | 9/1998 |
| JP | 3011898 | B2 | 2/2000 |
| JP | 2003210581 | A | 7/2003 |
| JP | 2009533112 | A | 9/2009 |
| JP | 2009533192 | A | 9/2009 |
| JP | 2015517363 | A | 6/2015 |
| KR | 102007001 1466 | A | 1/2007 |
| KR | 1020070011466 | A | 1/2007 |
| WO | WO 03084502 | A1 | 10/2003 |
| WO | WO2006101975 | A1 | 9/2006 |
| WO | WO2007132217 | A1 | 11/2007 |
| WO | WO2011149436 | A1 | 1/2011 |
| WO | WO 2016115379 | A1 | 7/2016 |
| WO | WO2016174393 | A1 | 11/2016 |
| WO | WO2017079397 | A1 | 5/2017 |
| WO | WO 2017/109626 | A1 | 6/2017 |

OTHER PUBLICATIONS

Lavorini, F., et al., "Recent advances in capsule-based dry powder inhaler technology," Multidisciplinary Respiratory Medicine (2017) 12:11, pp. 1-7, DOI 10.1186/s40248-017-0092-5.
Office Action 1 and English translation for Chinese Patent Application No. 201880074793.8, dated Feb. 3, 2021.
Search Report and English translation for Chinese Patent Application No. 201880074793.8, dated Jan. 21, 2021.
First Office Action (and its English translation) issued for corresponding Japanese Patent Application 2020-528425, dated Jul. 12, 2022.
English abstract for JP2009533192A dated Jul. 29, 2015.
English abstract for JP2015517363A dated Jul. 29, 2015.
English abstract for JP2003210581A dated Jul. 29, 2015.
English abstract for JP1998234827A dated Jul. 29, 2015.
English abstract for JP2009533112A dated Jul. 29, 2015.
International search report issued for counterpart Chinese patent application No. PCT/CN2018/116942 dated Feb. 21, 2019.
Extended European Search Report dated Jul. 15, 2021 for counterpart European patent application No. 18881161.6.
English abstract for CN204501970U dated Jul. 29, 2015.
Office Action 1 and English translation for Chinese Patent Application No. 202210022797.X, dated Aug. 23, 2022.
Office Action 1 for counterpart European patent application No. 18881161.6, dated Jul. 5, 2023.
Office Action 1 for counterpart Korean patent application No. 10-2020-7 016443, dated Sep. 25, 2023, along with the English translation.

* cited by examiner

DRY POWDER INHALER

CROSS-REFERENCE TO RELATED APPLICATIONS

This application is a continuation of International Application No. PCT/CN2018/116942, filed on Nov. 22, 2018, which claims priority to Chinese Patent Application No. 201711177647.1, entitled "New Dry Powder Inhaler", filed on Nov. 21, 2017, both of which are hereby incorporated by reference in their entireties.

TECHNICAL FIELD

The invention belongs to the field of medical device, and relates to a new dry powder inhaler, especially relates to a capsule dry powder inhaler.

BACKGROUND

The use of dry powder inhalers (DPI) for the treatment of bronchiectasis is well known, wherein the DPI is usually driven by the patient's respiration and disperses the drug into inhalable powder by aerodynamic method.

The capsule dry powder inhaler is a well-known dry powder inhaler, which comprises a capsule chamber and an actuator for opening the capsule chamber. The opening of the capsule is mainly achieved by shearing force, acupuncture or cutting, wherein the acupuncture is the most common opening mechanism, such as the capsule inhaler disclosed in U.S. Pat. No. 8,196,578 B2.

For the capsule DPI of the acupuncture mechanism, the powder contained in the capsule is released by piercing the capsule during atomization. When the patient inhales to generate sufficient airflow, the capsule starts to rotate and vibrate in the capsule chamber. As the inspiratory flow increases, the rotate speed of the capsule will increase, thereby generating sufficient centrifugal force to release the powder from the capsule. Therefore, the capsule DPI also has the problem of insufficient inspiratory flow for patients with impaired ability to produce sufficient inspiratory flow, and is generally not recommended for children under 5 and patients with impaired respiratory function.

In addition, combination therapies involving different and complementary active ingredients are also known. Currently, not only two, but also three or four active ingredients combination therapies have emerged. Although combination products provide additional convenience for patients, some pharmaceutical active ingredients are difficult to formulate into a single combination product. For example, when formulated together, the active ingredients may chemically interact with each other to have a negative effect.

The applicant has found that a capsule dry powder inhaler provides an effective method to solve the above-mentioned problems. The capsule dry powder inhaler comprises at least two capsule chambers and actuators matching the number of capsule chambers, each capsule chamber is loaded with capsules containing different pharmacologically active ingredients. By mixing the powder released from the capsules in different capsule chambers, a combined inhalation medicinal product can be provided to the patient.

SUMMARY

First, this application provides a powder release device for inhalation administration, comprising:

a capsule chamber, which is a cylindrical chamber that can hold the capsule upright, and the top of the capsule chamber is open;

an actuator, which comprises a needle, mounted to be movable toward the side wall of the capsule chamber to puncture the capsule, and at least one part of the actuator is located outside of the dry powder inhaler for manipulation by the user;

a nozzle, with an outlet duct extending from the top to the bottom, a screen cover is mounted at the bottom of the outlet duct, the screen cover is embedded with a screen, and detachably connected to the top of the capsule chamber to cover the top of the capsule chamber;

wherein, the capsule chamber is provided at its bottom and/or side wall with a deflected intake duct group ventilating with the outside air, the deflected intake duct group comprises at least two deflected intake ducts which are arranged around the central axis of the capsule chamber, simultaneously deflect clockwise or counterclockwise, in order to provide a spiral airflow that flows upward from the deflected intake ducts when the user inhales.

Preferably, the deflected intake ducts of the deflected intake duct group have the same shape and size, and are evenly arranged around the central axis of the capsule chamber.

Preferably, the lower side of the screen protrudes toward the capsule chamber.

Preferably, the bottom of the capsule chamber is provided with intake ducts opened upward and ventilating with the outside air to provide air flow from bottom to top.

Preferably, the capsule chamber is provided at the bottom or the lower part of the side wall thereof with intake ducts, which are opened upward and ventilating with the outside air to provide a through airflow from bottom to top, and the capsule chamber is provided at the bottom and/or the side wall thereof with a deflected intake duct group to provide a spiral airflow rotating around the capsule chamber.

Further preferably, the intake duct at the bottom of the capsule chamber is opened upward along the central axis of the capsule chamber.

Further preferably, the intake ducts at the bottom of the capsule chamber form a deflected intake duct group.

Further preferably, the deflected intake duct group is arranged at the bottom as a fixed impeller as a whole.

Further preferably, the opening of the deflected intake ducts is tangent to the side wall of the capsule chamber.

Preferably, the side wall of the capsule chamber is provided with a deflected intake duct group.

Further preferably, the lower and/or middle part of the side wall of the capsule chamber is provided with a deflected intake duct group.

Further preferably, the lower part of the side wall of the capsule chamber is provided with a deflected intake duct group.

Further preferably, the opening of the deflected intake duct is tangent to the side wall of the capsule chamber.

Further preferably, the opening of the deflected intake duct of the side wall of the capsule chamber has a long-strip shape, which is arranged longitudinally along the side wall of the capsule chamber.

Further preferably, the opening of the deflected intake duct of the side wall of the capsule chamber has a long-strip shape parallel to the central axis of the capsule chamber.

Preferably, a deflected intake duct group composed of two deflected intake ducts is provided in the lower part and/or the middle of the side wall of the capsule chamber, and an intake duct is provided at the bottom of the capsule chamber.

Preferably, a deflected intake duct group composed of two deflected intake ducts is provided at the lower part of the side wall of the capsule chamber and a direct intake duct is provided at the bottom of the capsule chamber.

Preferably, the diameter of the capsule chamber is 1.1 to 2.5 times that of the capsule, and the height of the capsule chamber is 1.02 to 2.0 times that of the capsule.

Further preferably, the diameter of the capsule chamber is 1.2 to 1.5 times that of the capsule, and the height of the capsule chamber is 1.05 to 1.3 times that of the capsule.

In a specific embodiment of this application, the diameter of the capsule chamber is 1.35 times that of the capsule and the height of the capsule chamber is 1.15 times that of the capsule.

Preferably, the side wall of the capsule chamber is provided with a first deflected intake duct group, and the bottom of the capsule chamber is provided with a second deflected intake duct group.

In another aspect, this application provides a method for releasing inhalable powder, comprising the following steps:

(1) Pack the capsule into a cylindrical capsule chamber that can hold the capsules upright;

(2) Cover the screen cover to the top of the capsule chamber, so that the nozzle is connected to the top of the capsule chamber through its outlet duct below it;

(3) Puncture the capsule;

(4) Inhale at the nozzle to create the following airflow in the capsule chamber: a) bottom-to-top through airflow that enters through the intake duct at the bottom of the capsule chamber or the deflected intake duct group at the lower part of the side wall and exits from the top of the capsule chamber; b) a spiral airflow that enters through the deflected intake duct group at the bottom and/or side wall of the capsule chamber and exits from the top of the capsule chamber, the through airflow and the spiral airflow together promote the rotation and vibration of the capsule in the capsule chamber to release the inhalable powder.

Preferably, in the step (4), inhale at the nozzle to create the following airflow in the capsule chamber: a) a bottom-to-top through airflow that enters through the intake duct at the bottom of the capsule chamber and exits from the top of the capsule chamber and b) a spiral airflow that enters through the deflected intake duct group through the side wall of the capsule chamber and exits from the top of the capsule chamber, the through airflow and the spiral airflow together promote the rotation and vibration of the capsule in the capsule chamber to release the inhalable powder.

Preferably, this application provides a method for releasing the inhalable powder in the capsule using the powder release device as described in the first part.

The method for releasing inhalable powder of this application can create a spiral airflow when the user inhales, which reduces the starting flow rate of the capsule to release the inhalable powder, enables the user to provide less inspiratory flow to allow the capsule to rotate and vibrate at high speed to release the drug power, and provides a way for children under 5 and patients with impaired respiratory function to use capsule DPI.

The powder release device of this application can create a spiral air flow through a deflected intake duct in the capsule chamber when the user inhales, which reduces the starting flow rate of the rotation, allows the user to provide less inspiratory flow to make the capsule rotate at high speed to release the drug, and provides a way for children under 5 years of age and patients with impaired respiratory function to use capsule DPI.

In a third aspect, this application provides a dry powder inhaler, comprising:

capsule chambers, which are cylindrical chambers that can hold the capsule upright, the top of the capsule chambers is open, and the bottom and/or the side walls of the capsule chambers are provided with intake ducts ventilating with the outside air;

actuators, comprising puncture needles, mounted for the user to operate to move toward the side walls of the capsule chambers to puncture the capsules;

nozzle, comprising an outlet duct under the nozzle;

wherein, the number of the capsule chambers is two to four, and all the capsule chambers are arranged in parallel to form an integral multi-capsule chamber, the actuators are mounted individually or in common among the capsule chambers, and the actuators are mounted with needles in the width direction of the actuators, at least the number of the needles is same as that of matching capsule chambers, a screen cover is mounted at the bottom of the outlet duct under the nozzle, and a screen is fixed in the screen cover, and separately connected to the top of the multi-capsule chamber, making the screen cover the top of all of the capsule chambers.

Preferably, the side wall of the outlet duct is provided with at least one small hole ventilating with the outside air, and the small hole is opened in a direction not facing the central axis of the outlet duct to promote airflow rotate in the outlet duct when the user inhales.

Preferably, the diameter of the outlet duct gradually decreases from bottom to top, and a narrow neck is formed before arriving at the nozzle, and the small hole of the outlet duct is provided at the lower side of the narrow neck.

Further preferably, the number of the small holes in the side wall of the outlet duct is two, the two small holes are symmetrically opened around the central axis of the outlet duct.

Preferably, an intake duct is provided at the bottom of each capsule chamber to provide air flow from bottom to top when the user inhales. The intake duct opens upward and ventilates with outside air.

Further preferably, the intake duct at the bottom of each capsule chamber comprises a deflected intake duct group, the deflected intake duct group comprises at least two deflected intake ducts which are arranged around the central axis of the capsule chamber, simultaneously deflect clockwise or counterclockwise, in order to provide a spiral airflow that flows upward from the bottom when the user inhales.

Further preferably, the intake ducts at the bottom of each capsule chamber is a deflected intake duct group, the deflected intake duct group comprises at least two deflected intake ducts which are arranged around the central axis of the capsule chamber, simultaneously deflect clockwise or counterclockwise, in order to provide a spiral airflow that flows upward from the bottom when the user inhales.

Further preferably, the deflected intake ducts of the deflected intake duct group of each capsule chamber have the same shape and size, and are evenly arranged around the central axis of the capsule chamber.

Further preferably, the opening of the deflected intake ducts at the bottom of the capsule chamber is tangent to the side wall of the capsule chamber.

In a specific embodiment of this application, the deflected intake duct at the bottom of each capsule chamber is arranged as a fixed impeller as a whole.

Preferably, the side wall of each capsule chamber is provided with a deflected intake duct group, the deflected intake duct group comprises at least two deflected intake ducts which are arranged around the central axis of the capsule chamber, simultaneously deflect clockwise or counterclockwise, in order to provide a spiral airflow that flows upward from the bottom when the user inhales.

Further preferably, the deflected intake duct group is provided in the middle and/or lower part of the side wall of the capsule chamber.

Further preferably, the deflected intake duct group is provided at the lower part of the side wall of the capsule chamber.

Further preferably, the deflected intake ducts in a deflected intake duct group have the same shape and size, and are evenly arranged around the central axis of the capsule chamber.

Further preferably, the opening of the deflected intake duct is tangent to the side wall of the capsule chamber.

Further preferably, the opening of the deflected intake duct of the side wall of the capsule chamber has a long-strip shape, which is arranged longitudinally along the side wall of the capsule chamber.

Further preferably, the opening of the deflected intake duct of the side wall of the capsule chamber has a long-strip shape parallel to the central axis of the capsule chamber.

Further preferably, the number of deflected intake ducts of a deflected intake duct group is two.

In a specific embodiment of this application, a deflected intake duct group composed of two deflected intake ducts is provided at the lower part of the side wall of the capsule chamber, and an intake duct is provided at the bottom of the capsule chamber.

Preferably, the size of the intake duct and/or top opening of at least one capsule chamber is different from that of other capsule chambers, so that the air flow rate in the capsule chamber is different from that of the other capsule chambers.

Further preferably, the size of the intake duct of at least one capsule chamber is different from that of other capsule chambers, so that the air flow rate in the capsule chamber is different from that of the other capsule chambers.

Preferably, the diameter of the capsule chamber is 1.1 to 2.5 times the diameter of the capsule, and the height of the capsule chamber is 1.02 to 2.0 times the height of the capsule.

Further preferably, the diameter of the capsule chamber is 1.2 to 1.5 times the diameter of the capsule, and the height of the capsule chamber is 1.05 to 1.3 times the height of the capsule.

In a specific embodiment of the invention, the diameter of the capsule chamber is 1.35 times the diameter of the capsule and the height of the capsule chamber is 1.15 times the height of the capsule.

Preferably, the multi-capsule chamber is composed of a first capsule chamber and a second capsule chamber, a first actuator and a second actuator are arranged at both ends of the connecting line where the first capsule chamber and the second capsule chamber are located, the first actuator and the second actuator can move from both sides to the middle so as to puncture the capsules in the first capsule chamber and the second capsule chamber, respectively.

Preferably, the multi-capsule chamber is composed of first capsule chamber and a second capsule chamber, which are closely arranged, a first actuator and a second actuator are arranged at both ends of a line connecting the first capsule chamber and the second capsule chamber, the first actuator and the second actuator can move from both sides to the middle so as to puncture the capsules in the first capsule chamber and the second capsule chamber, respectively.

Preferably, the multi-capsule chamber is composed of first capsule chamber and second capsule chamber, which are closely arranged, and an actuator is arranged on one side of the line connecting the first capsule chamber and the second capsule chamber, the actuator comprises at least two needles in the width direction to puncture the capsules in the first capsule chamber and the second capsule chamber at the same time.

Further preferably, the lower part of the outlet duct is divided by a central baffle to form a first sub-duct and a second sub-duct, which are respectively connected to the tops of the first capsule chamber and the second capsule chamber, the first sub-duct and the second sub-duct gradually gather from bottom to top from the top of each capsule chamber toward the central baffle, their cross-sections gradually narrow or maintain, they direct the airflows of the first capsule chamber and the second capsule chamber converge to the upper part of the outlet duct, along the first sub-duct and the second sub-duct respectively, when the user inhales. More preferably, the cross-sections of the first sub-duct and the second sub-duct gradually narrow from the top of each capsule chamber first, and then remain.

Further preferably, the cross-section of the outlet duct maintains the same size or gradually increases from the top of the central baffle toward the nozzle. Further preferably, the cross-sections of the outlet ducts gradually increase in a direction from the top of the central baffle toward the nozzle first, and then remain.

More preferably, the first sub-duct and the second sub-duct further comprise one or more sub-baffles, the one or more sub-baffles divide the first sub-duct and the second sub-duct to narrower ducts respectively, which gradually gather from bottom to top from the top of each capsule chamber toward the central baffle. More preferably, the height of the sub-baffle is lower than that of the central baffle. More preferably, the whole shape of the cross-section of the sub-baffles is like "X", which takes the central baffle as the plane mirror symmetry.

Further preferably, the nozzle is mounted at where the airflow from the first capsule chamber and the second capsule chamber has fully converged in the upper part of the outlet duct along the first sub-duct and the second sub-duct respectively when the user inhales.

More preferably, the length of the outlet duct is 25-36 mm, most preferably 31 mm.

Further preferably, the air resistance of the dry powder inhaler is 0.01-0.08 KPa 0.5 minutes/liter.

More preferably, the air resistance of the dry powder inhaler is 0.02-0.05 KPa 0.5 minutes/liter.

In a specific embodiment of this application, the air resistance of the dry powder inhaler is 0.0325 KPa 0.5 minutes/liter.

Preferably, the multi-capsule chamber is closely arranged into a triangle by the first capsule chamber, the second capsule chamber and the third capsule chamber, and a first actuator is arranged on one side of the line connecting the first capsule chamber and the second capsule chamber, the first actuator comprises at least two needles in the width direction to puncture the capsules in the first capsule chamber and the second capsule chamber at the same time, a second actuator is arranged on the side of the third capsule chamber that far away from the first capsule chamber and the second capsule chamber, it is movable in a vertical direction of the straight line where the first capsule chamber and the second capsule chamber are located to puncture the capsule in the third capsule chamber.

Further preferably, the air resistance of the dry powder inhaler is 0.015-0.073 KPa 0.5 minutes/liter.

More preferably, the air resistance of the dry powder inhaler is 0.02-0.04 KPa 0.5 minutes/liter.

In a specific embodiment of this application, the air resistance of the dry powder inhaler is 0.0305 KPa 0.5 minutes/liter.

Preferably, the multi-capsule chamber is closely arranged into a square by the first capsule chamber, the second capsule chamber, the third capsule chamber and the fourth capsule chamber, and a first actuator and a second actuator are arranged on the central axes of the square and movable from both sides to the middle, the first actuator and the second actuator comprise at least two needles in the width direction, so that the first actuator punctures the capsules in the capsule chamber and the second capsule chamber at the same time, the second actuator punctures the capsules in the third capsule chamber and the fourth capsule chamber at the same time.

Further preferably, the air resistance of the dry powder inhaler is 0.01-0.06 KPa 0.5 minutes/liter.

Even more preferably, the air resistance value of the dry powder inhaler is 0.015-0.035 KPa 0.5 minutes/liter.

In a specific embodiment of this application, the air resistance of the dry powder inhaler is 0.029 KPa 0.5 minutes/liter.

Preferably, the dry powder inhaler comprises:

a lower casing, which defines a cavity, the tope of which is open and is used for accommodating a multi-capsule chamber inside, the side of the lower casing is provided with gaps that match the number and position of the actuators, so that part of each actuator is located outside the dry powder inhaler for the user to operate, and the cavity ventilates with the outside air;

an adapter plate, which covers the top of the lower casing, and a hollow port is provided at the top of the multi-capsule chamber, a screen cover is detachably mounted to the hollow port so that the screen can cover the top of each capsule chamber through the hollow port;

an upper casing, which extends downward from the top of the nozzle, defines a cavity surrounding the outlet duct and the bottom of the cavity being open, and covers the adapter plate when the screen cover is mounted at the hollow port.

Preferably, the dry powder inhaler comprises:

a lower casing, which defines a cavity, the tope of which is open and is used for accommodating a multi-capsule chamber inside, the side of the lower casing is provided with gaps, the number and position of which match with the number and position of the actuators, so that at least one part of each actuator is located outside the dry powder inhaler for the user to operate, and the cavity ventilates with the outside air through an air intake hole provided on the side and/or at the bottom of the lower casing;

a adapter plate, which covers the top of the lower casing, and a hollow port is provided at the top of the multi-capsule chamber, a screen cover is detachably mounted to the hollow port so that the screen can cover the top of each capsule chamber through the hollow port;

an upper casing, which extends downward from the top of the nozzle, defines a cavity surrounding the outlet duct and the bottom thereof being open, and covers the adapter plate when the screen cover is mounted at the hollow port.

Preferably, the multi-capsule chamber is formed integrally with the adapter plate, which is fixed below the hollow port of the adapter plate.

Preferably, the gaps are widened and/or extended based on the size of the actuator to provide the air intake hole.

Preferably, the side wall of the outlet duct is provided with at least one small hole ventilating with the outside air, and the small hole is opened in a direction not facing the central axis of the outlet duct to promote airflow rotate in the outlet duct when the user inhales.

Preferably, the upper casing, the lower casing and the adapter plate are connected together by a hinge on the same side.

Preferably, the adapter plate and the capsule chamber are integrally formed, and the hollow port constitutes the top opening of each capsule chamber.

Preferably, the diameter of the outlet duct gradually decreases from bottom to top, and a narrow neck is formed before arriving at the nozzle.

Preferably, a slit or a hole is provided at the junction of the upper casing and the adapter plate, so that the cavity can ventilate with the outside air through the slit or the hole;

Further preferably, the number of small holes on the outlet duct is two, the two small holes are symmetrically opened around the central axis of the outlet duct.

Further preferably, the small holes on the outlet duct are located in the area below the narrow neck.

The dry powder inhaler of this application provides a medicine dispenser containing different active components (or a mixture thereof) separately by providing a plurality of capsule chambers arranged in parallel. The structure is simple and the operation is convenient. In addition, each capsule chamber can adjust the parameters of the intake duct and the air exhaust duct according to the nature of the powder of the drug (composition), in order to provide suitable particle distribution for each active ingredient.

DETAILED DESCRIPTION OF THE EMBODIMENTS

The present invention will be further described below in conjunction with specific embodiments. However, it should not be understood that the scope of the above subject of this application is only limited to the following embodiments, and any technology implemented based on the content of this application belongs to the scope of this application.

Figure 1:
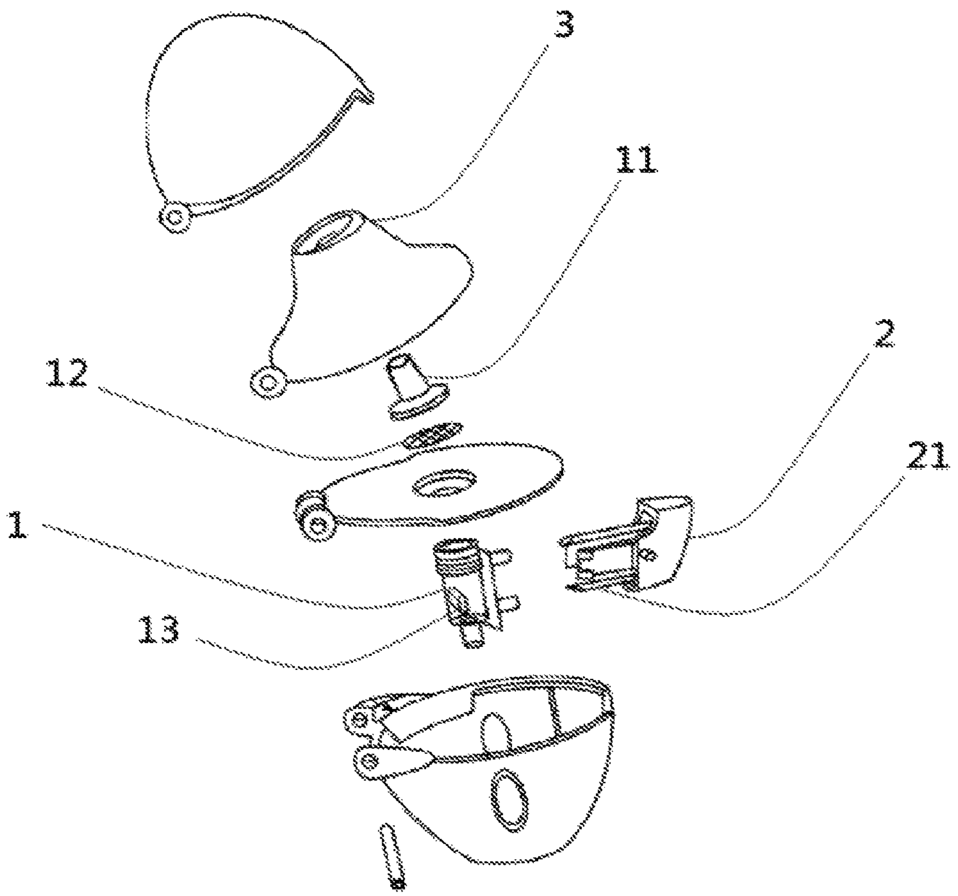
FIG. 1 shows a disassembled view of the structure of a powder release device of this invention.
Figure 2:
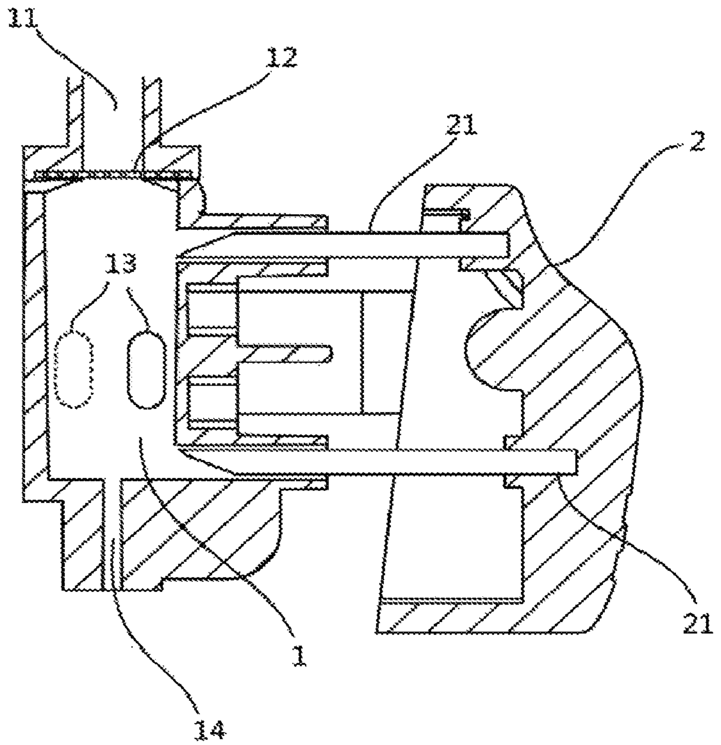
FIG. 2 shows a sectional view of a capsule chamber of the powder release device shown in FIG. 1
Figure 3:
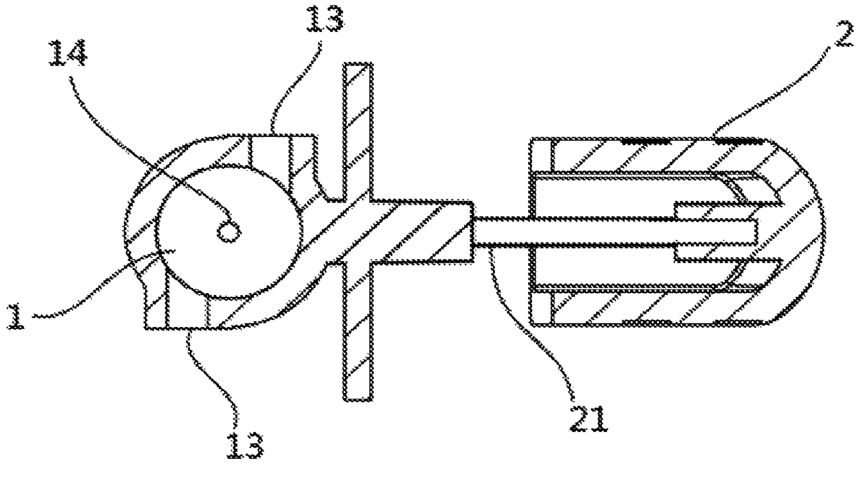
FIG. 3 shows a cross-sectional top view of the capsule chamber shown in FIG. 2.

By referring to FIG. 1, FIG. 2 and FIG. 3, FIG. 1 illustrates a specific embodiment of a powder release device of the present invention, comprising: (a) a capsule chamber 1, which is a cylindrical chamber that can receive the capsule, the capsules chamber 1 is provided with an outlet duct 11 at the top thereof, and a ventilating screen 12 is mounted at the junction of the outlet duct 11 and the capsule chamber 1; (b) the actuator 2, which comprises at least one needle 21, which is mounted as it can move to the capsule chamber 1 to puncture the capsule, and at least one part of the actuator 2 is located outside the powder release device for the user to manipulate; (c) the nozzle 3, which is connected to the top of the capsule chamber 1 through the outlet duct 11. By referring to FIG. 2, the capsule chamber 1 is provided with a deflected intake duct group that ventilates with outside air. By referring to, the deflected intake duct group comprises at least two deflected intake ducts 13, which are arranged around the central axis of the capsule chamber and simultaneously deflect clockwise or counterclockwise, in order to provide a spiral airflow that flows from the deflected intake duct group to the top outlet duct 11 when the user inhales.

In this embodiment, the user opens the screen 12 mounted above the capsule chamber 1 first and puts the capsule herein, then presses the actuator 2 to puncture the capsule, and the actuator 2 is then reset by manual operations or elastic means. Since the nozzle 3 ventilates with the capsule chamber 1 through an outlet duct 11, and the capsule chamber 1 ventilates with the external environment through the deflected intake duct group, when the user inhales, the outside air passes through the deflected intake duct group to generate a spiral airflow surrounding the capsule chamber 1, to promote a rapid rotation of the punctured capsule to release the inhalable medicinal powder contained therein. The inhalable medicinal powder moves with the airflow to the outlet duct 11 at the top of the capsule chamber 1 and enters the user's body through the nozzle 3.

It should be noted that the deflected intake duct 13 of this embodiment is deflected clockwise or counterclockwise, but it does not mean that the deflected intake duct group must be opened in the horizontal direction, as long as it can provide a part of the air flow deflected in the horizontal direction. Of course, the at least two deflected intake ducts 13 should be deflected simultaneously. For example, when the deflected intake passages 13 are located on the side wall, they should all face diagonally upward, all face diagonally downward, or all face horizontally.

Compared with the prior art, the powder release device of this embodiment provides the deflected intake duct group in the capsule chamber 1, so that the requirement of the user's inhalation flow when the capsule rotates and releases medicine is greatly reduced, the powder is easier to release and the amount of residue reduces.

The deflected intake ducts 13 of the deflected intake duct group have the same shape and size, and are evenly arranged around the central axis of the capsule chamber 1 to provide more uniform spiral airflow. Since the release of the inhalable powder in the capsule is achieved by the rotation and vibration of the capsule in the capsule chamber 1, but not based on only the rotation, the shapes and sizes of the deflected intake ducts 13 of the deflected intake duct group do not have to be exactly the same.

Compared with the prior art, the powder release device of this embodiment provides the deflected intake duct group in the capsule chamber 1, so that the requirement of the user's inhalation flow rate when the capsule rotates and vibrates to release medicine is greatly reduced, the powder is easier to release and the amount of residue is reduced.

Further preferably, by referring to FIG. 1, in one embodiment, the lower side of the ventilating screen 12 protrudes toward the capsule chamber 1, and this shape can provide a capsule rotating contact surface with less resistance.

Further preferably, by referring to FIG. 2 and FIG. 3, in one embodiment, the deflected intake duct group is provided on the side wall of the capsule chamber 1, and the bottom of the capsule chamber 1 is also provided with an intake duct 14 ventilating with the outside air, which is opened upwards along the central axis of the capsule chamber 1 to provide an air flow throughout the capsule chamber 1 from bottom to top when the user inhales.

In this embodiment, the intake duct 14 at the bottom of the capsule chamber 1 can provide a through airflow throughout the entire capsule chamber 1 from bottom to top when the user inhales, in order to help the top of the capsule to rotate against the ventilating screen 12 at the top of the capsule chamber 1, so that the powder released from the capsules moves toward the top of the outlet duct 11 more smoothly.

In this embodiment, the opening of the deflected intake duct 13 at the side wall of the capsule chamber 1 has a long-strip shape, which is arranged longitudinally along the side wall of the capsule chamber, in order to provide an airflow having a larger surface contact with the capsule when the user inhales, so as to drive the capsule to rotate and vibrate easier in the capsule chamber 1 to release the inhalable powder.

Further preferably, by referring to FIG. 2 and FIG. 3, in one embodiment, the opening of the deflected intake duct 13 at the side wall of the capsule chamber 1 has a long-strip shape which is parallel to the central axis of the capsule chamber, so that when the user inhales, an airflow with a larger surface contact with the capsule and a better applying force direction is provided to drive the capsule to rotate and vibrate more smoothly in the capsule chamber 1 so as to release the inhalable powder.

Figure 4:
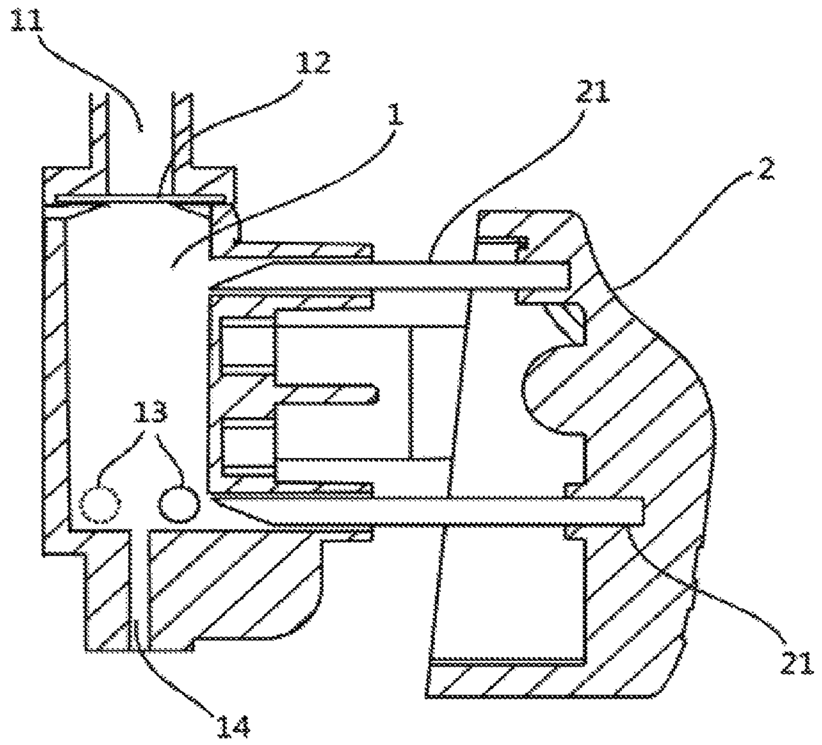
FIG. 4 shows another sectional view of the capsule chamber of the powder release device shown in FIG. 1.
Figure 5:
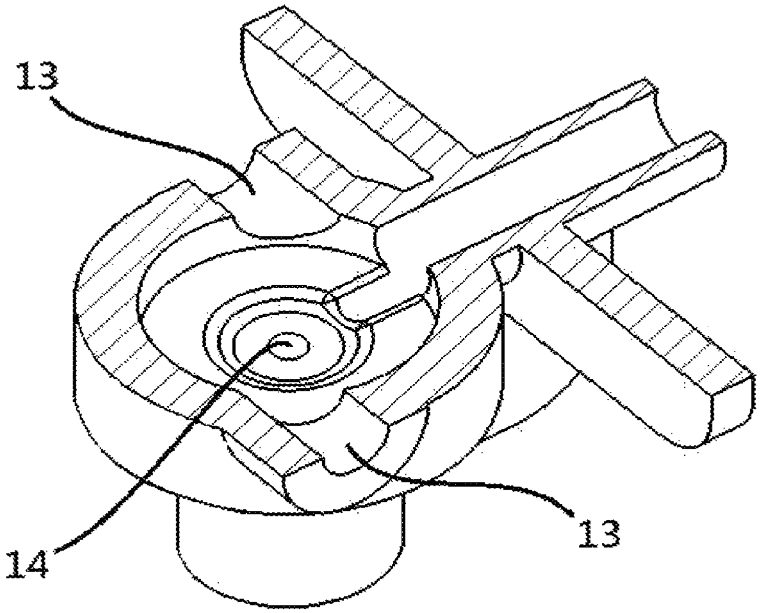
FIG. 5 shows a structural view of the lower part of the section of the capsule chamber shown in FIG. 4.

Further preferably, by referring to FIG. 4 and FIG. 5, in one embodiment, the deflected intake duct group is provided at the lower part of the side wall of the capsule chamber 1, and the intake duct 14 is provided at the bottom of the capsule chamber 1, wherein the intake duct is opened upwards along the central axis of the capsule chamber 1 to provide an air flow throughout the capsule chamber 1 from bottom to top when the user inhales.

The deflected intake duct group is provided at the lower part of the side wall of the capsule chamber 1, which can better provide a through airflow throughout the entire capsule chamber 1 from bottom to top when the user inhales, in order to help the top of the capsule to rotate against the ventilating screen 12 at the top of the capsule chamber 1, so that the powder released from the capsule moves toward the top of the outlet duct 11 more smoothly.

Figure 6:
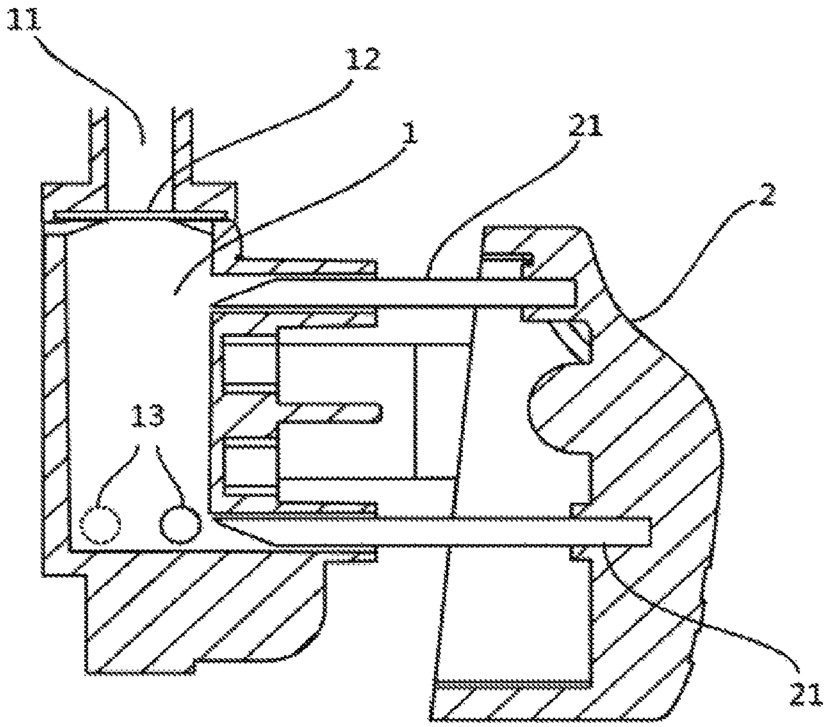
FIG. 6 shows another sectional view of the capsule chamber of the powder release device shown in FIG. 1.
Figure 7:
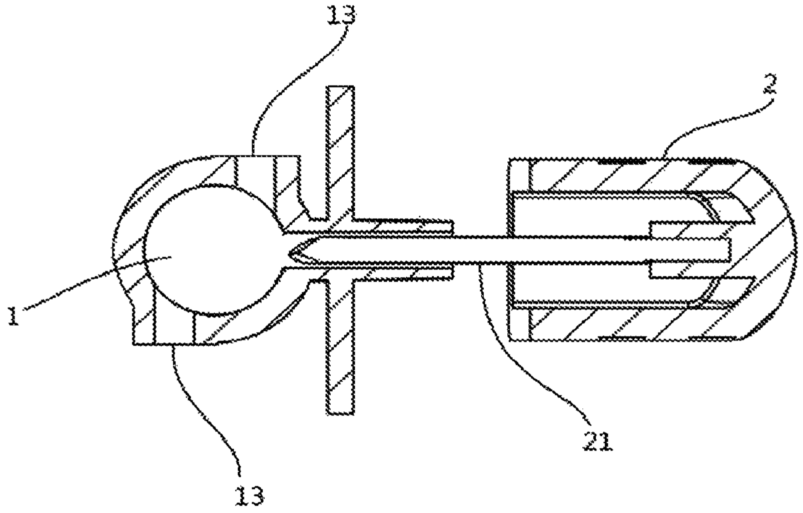
FIG. 7 shows a sectional top view of the capsule chamber shown in FIG. 6.

Further preferably, by referring to FIG. 6 and FIG. 7, in one embodiment, the deflected intake duct group is provided at the lower part of the side wall of the capsule chamber 1, and the intake duct 14 is not provided at the bottom of the capsule chamber 1.

The deflected intake duct group is only provided at the lower part of the side wall of the capsule chamber 1, which can also provide a bottom-up airflow when the user inhales, in order to help the top of the capsule to rotate against the ventilating screen 12 at the top of the capsule chamber 1. It can be understood that, in order to make the top of the capsule rotate against the screen 12 at the top of the capsule chamber 1, the through airflow is not necessary, as long as a non-through airflow from bottom to top is enough to lift the capsule.

Figure 8:
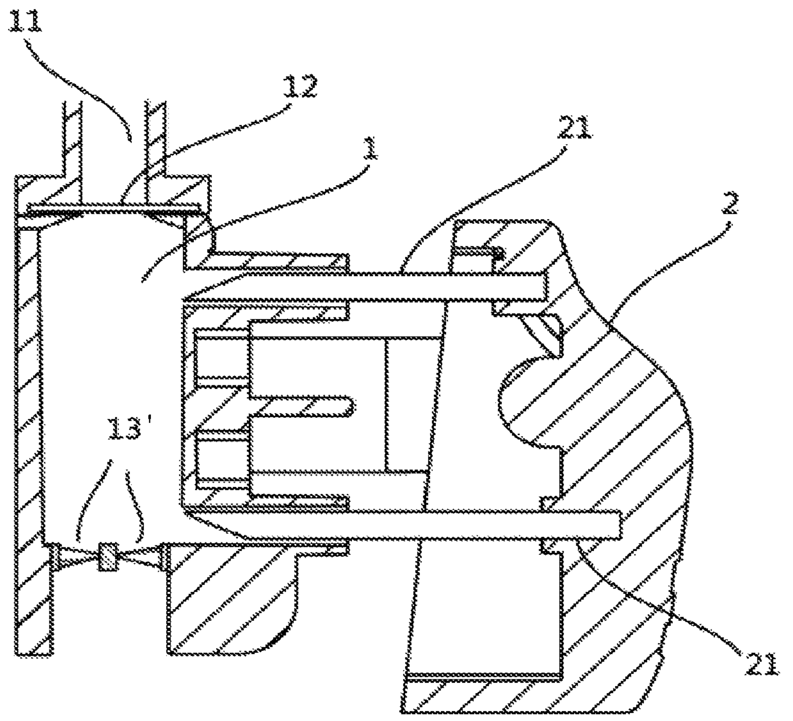
FIG. 8 shows another sectional view of the capsule chamber area of the powder release device shown in FIG. 1.
Figure 9:
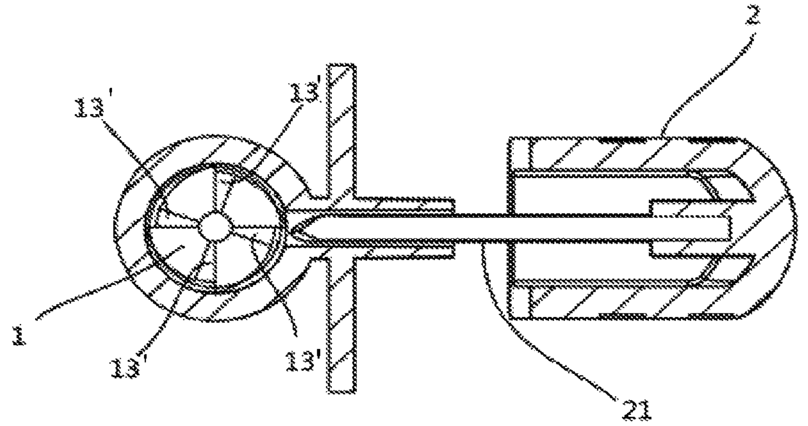
FIG. 9 shows a sectional top view of the capsule chamber shown in FIG. 8.
Figure 10:
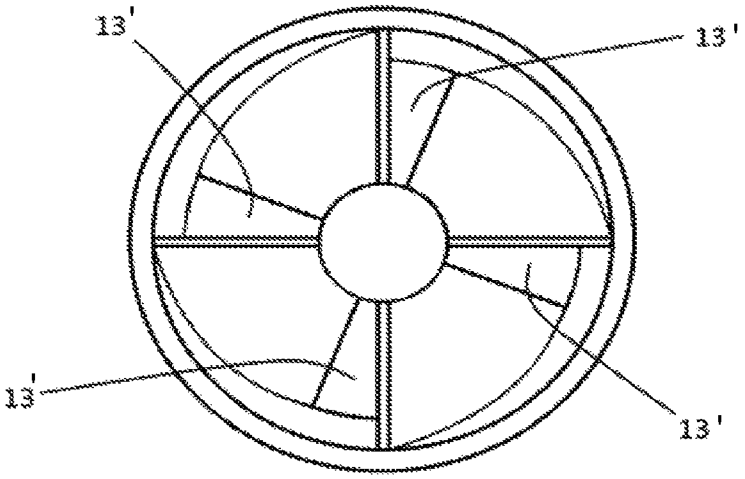
FIG. 10 is a partially enlarged view of the impeller at the bottom of the capsule chamber shown in FIG. 9.

By referring to FIG. 8, FIG. 9 and FIG. 10, in another embodiment of a powder release device of the present invention, a deflected intake duct group is provided at the bottom of the capsule chamber 1.

In this embodiment, the deflected intake duct group at the bottom of the capsule chamber 1 can also be evenly arranged around the central axis of the capsule chamber, simultaneously deflect clockwise or counterclockwise. When the user inhales, it can provide a part of the spiral airflow that is deflected in the horizontal direction to help the capsule rotate and vibrate to release the inhalable powder, and it can also provide another part of the bottom-to-up through airflow to help the top of the capsule rotate against the ventilating screen 12 at the top of the capsule chamber 1, so that the powder released from the capsule moves towards the top of the outlet duct 11 more smoothly. The structure is simple, and it serves two purposes.

Further preferably, by referring to FIG. 9 and FIG. 10, in one embodiment, the deflected intake duct group at the bottom is arranged as a fixed impeller as a whole.

In this embodiment, the deflected intake duct group of the impeller structure at the bottom of the capsule chamber 1 can be understood as being composed of four deflected intake ducts 13' separated by four blades.

Figure 11:
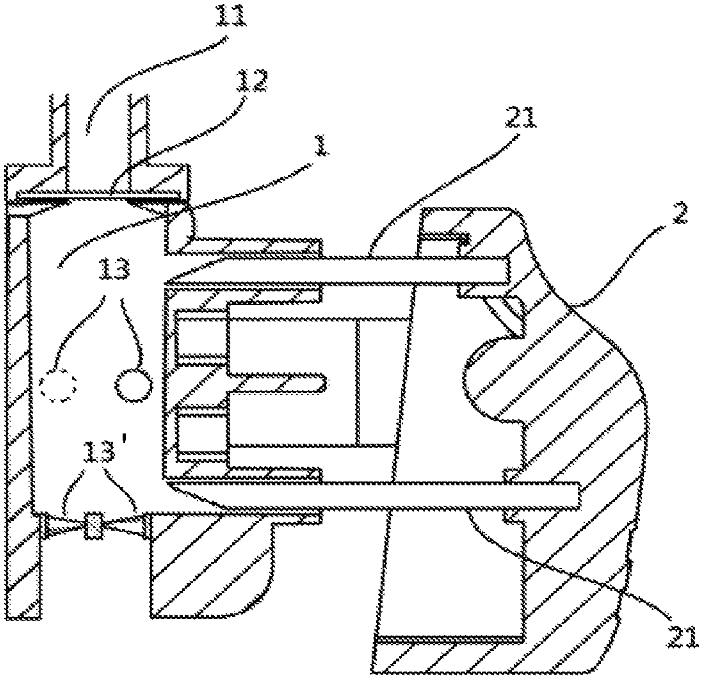
FIG. 11 is a sectional view of another capsule chamber area of the powder release device shown in FIG. 1.
Figure 12:
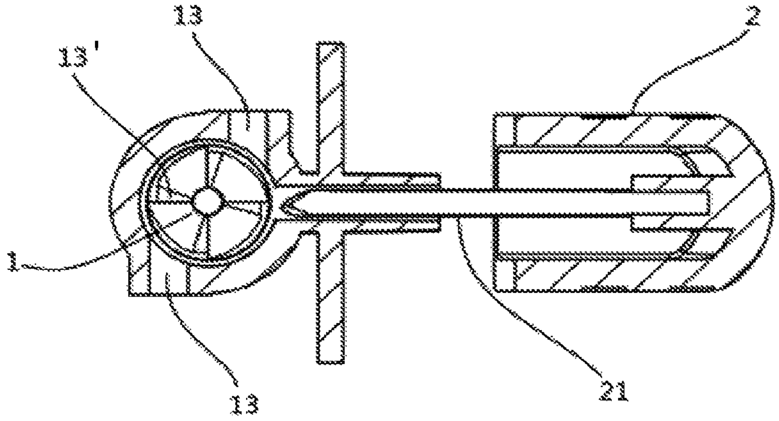
FIG. 12 shows a sectional top view of the capsule chamber area shown in FIG. 11.

Further preferably, by referring to FIG. 11 and FIG. 12, in one embodiment, each of the bottom and side walls of the capsule chamber 1 is provided with a deflected intake passage group.

In this embodiment, each of the deflected intake duct groups at the bottom of the capsule chamber 1 and those at the side wall serve to provide deflected airflow, wherein the deflected intake duct groups at the bottom of the capsule chamber 1 can also provide a bottom-up through airflow, and the object of the present invention can also be achieved.

Figure 13:
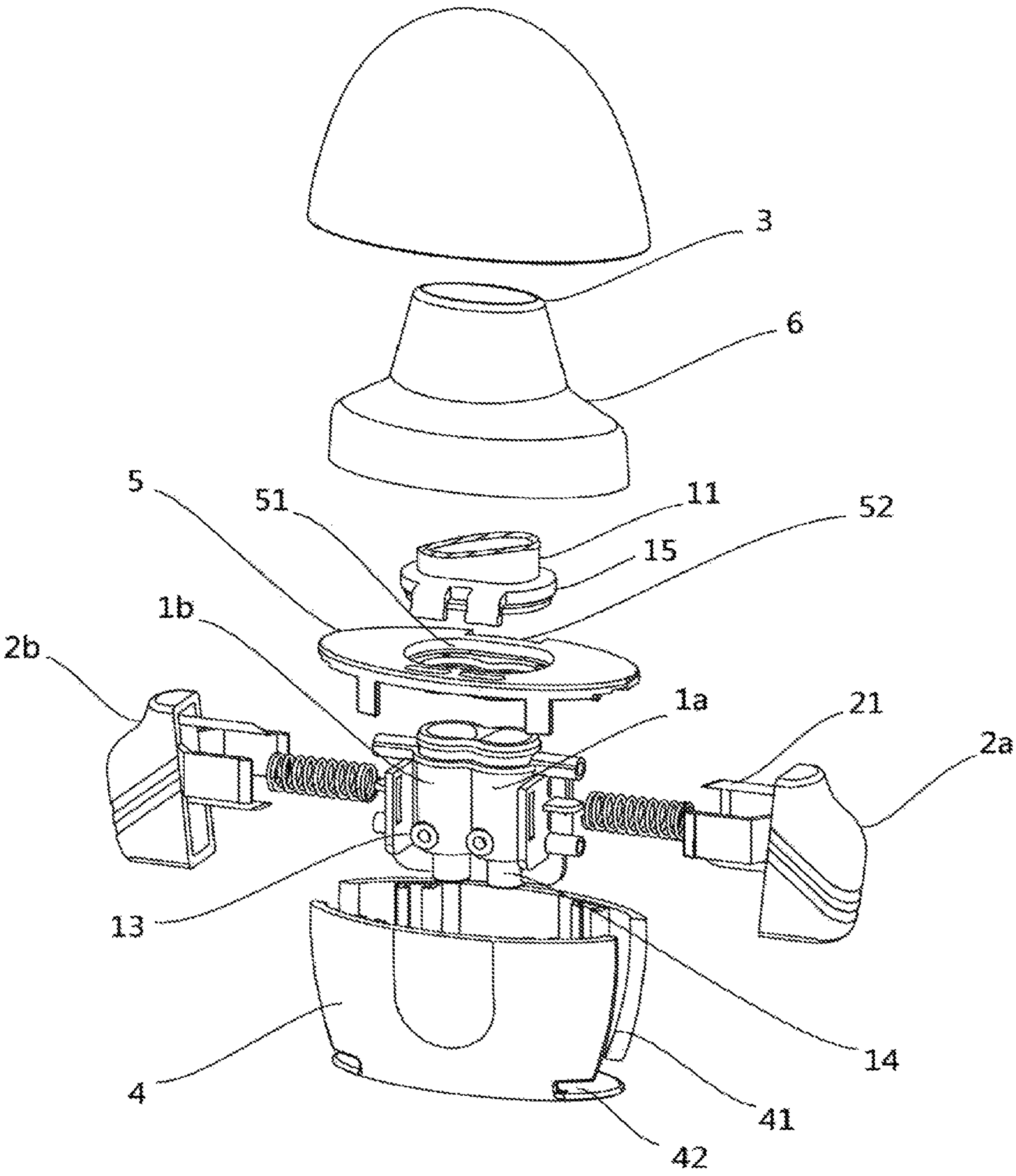
FIG. 13 shows a disassembled view of the structure of a dry powder inhaler of the present invention.
Figure 14:
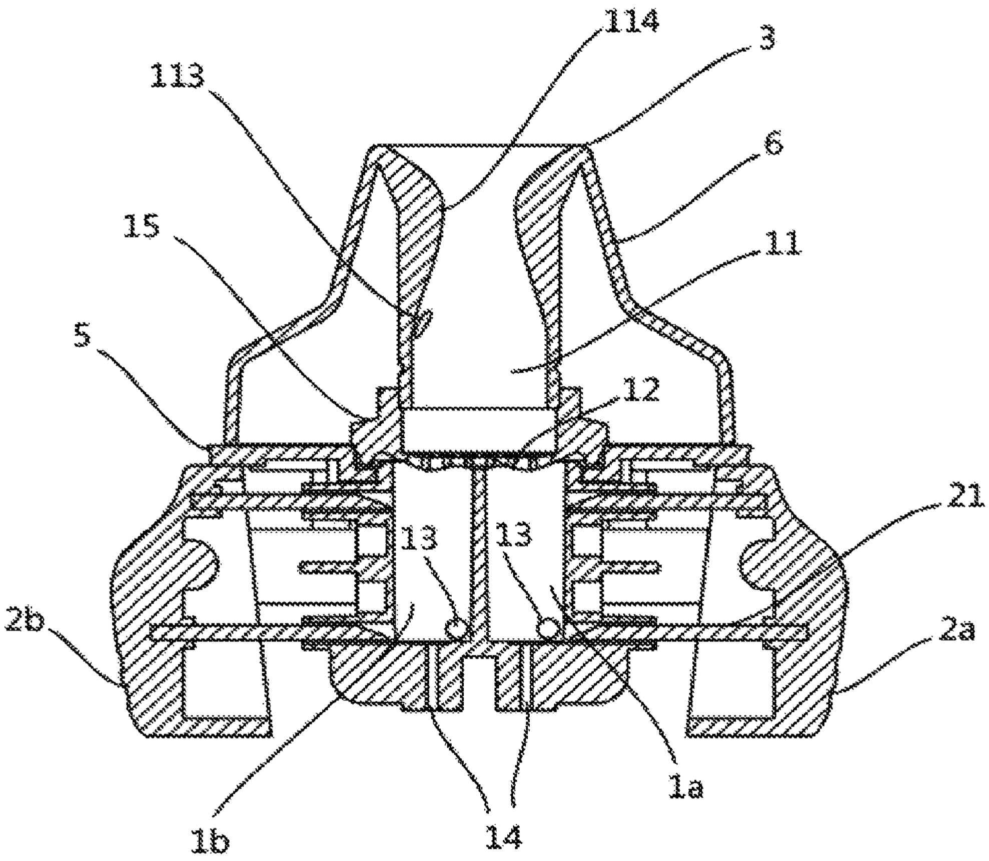
FIG. 14 is a partial cross-sectional view of the dry powder inhaler shown in FIG. 13.

By referring to FIG. 13 and FIG. 14, it is an embodiment of a dry powder inhaler of the present invention, comprising: (a) capsule chambers 1 (that is, 1*a* and 1*b* in the FIG.), which are cylindrical chambers that can hold a capsule upright, the top of the capsule chambers 1 is open, and the bottom of the capsule chambers 1 is provided with intake ducts 14 that ventilate with the outside air; (b) actuators 2, which comprise puncture needles 21, the puncture needles 21 are mounted for the user to operate to move toward the side walls of the capsule chambers 1 to puncture the capsules; (c) nozzle 3, illustrated in FIG. 13 and FIG. 15, which comprises an outlet duct 11 below the nozzle (for clarity, the lower part of the outlet 11 in FIG. 13 is intercepted and separated for display); wherein, the number of the capsule chambers 1 is two, the two capsule chambers 1 are arranged in parallel to form an integrally formed double-capsule chamber, and the actuators 2 are mounted individually between the capsule chambers 1, each actuator 2 is provided with two needles 21 in the height direction, a screen cover 15 is mounted at the bottom opening of the outlet duct 11, by referring to FIG. 16, a screen 12 is mounted in the screen cover 15 and can be separately connected to the top of the double-capsule chamber, so that the screen 12 covers the tops of the two capsule chambers 1.

In this embodiment, the double capsule-chamber is composed of first capsule chamber 1*a* and second capsule chamber 1*b* which are closely arranged, and the first actuator 2*a* and the second actuator 2*b* are arranged at both ends of the line where the first capsule chamber 1*a* and the second capsule chamber 1*b* are located, the first actuator 2*a* and the second actuator 2*b* can move from both sides to the middle so as to puncture the capsules in the first capsule chamber 1*a* and the second capsule chamber 1*b*, respectively.

The user separates the screen cover 15 from the top of the double-capsule chamber first, to make the top of the double-capsule chamber open; after filling the capsule chambers 1 with capsules containing different active ingredients, the screen cover 15 is closed to make the screen 12 cover the top of the capsule chambers 1 again; then, the user operates the actuators 2 to move from both sides to the middle so as to puncture the capsules in the first capsule chamber 1*a* and the second capsule chamber 1*b*, respectively, and the actuators 2 are reset by elastic components commonly used in the prior art; finally, the user covers the mouth to the nozzle 3 closely and inhales forcefully, and the outside air enters the capsule chambers through the intake duct 14 at the bottom of the capsule chambers 1, so that the capsules vibrate and rotate against the screen 12 to release the powder. The released powder from the capsules passes through the screen 12 into the outlet duct 11 and finally enters the human body.

Although the actuators 2 of this embodiment move from both sides to the middle so as to puncture the capsules in the first capsule chamber 1*a* and the second capsule chamber 1*b*, respectively, person skilled in the art can adjust the arrangement of the actuators, for example, the actuators 2 are provided on one side of the line where the first capsule chamber 1*a* and the second capsule chamber 1*b* are located, the actuators 2 comprise at least two needles in the width direction, so that when operated, the actuators 2 puncture the capsules in the first capsule chamber 1*a* and the second capsule chamber 1*b* at the same time.

Figure 17:
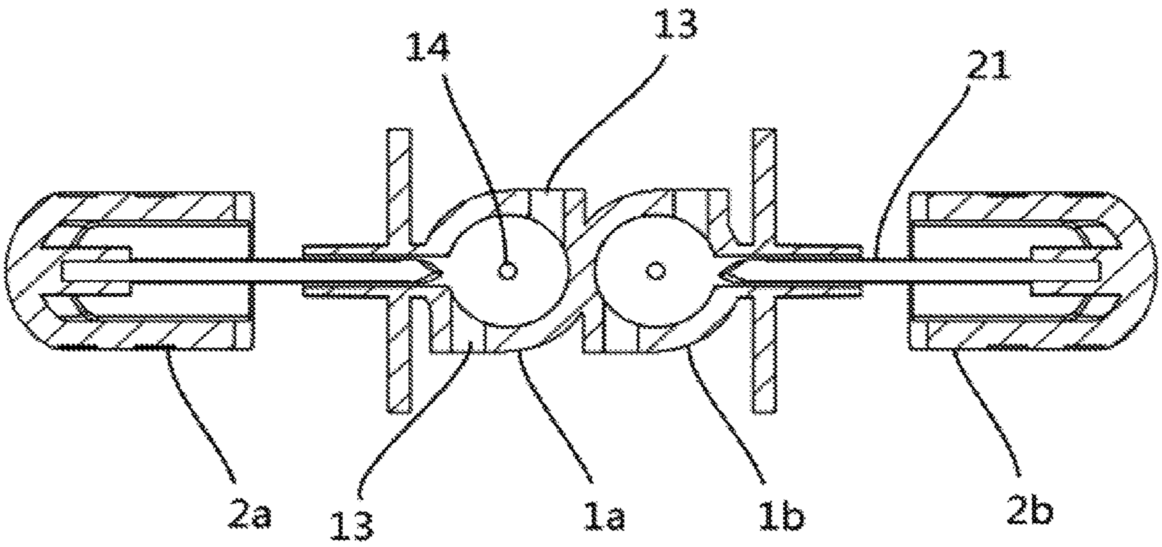
FIG. 17 shows a sectional plan view of the multi-capsule chamber of the dry powder inhaler shown in FIG. 13.

Further preferably, by referring to FIG. 17, in one embodiment, the side wall of each capsule chamber 1 is respectively provided with a deflected intake duct group. The deflected intake duct group comprises two deflected intake ducts 13 which are arranged around the central axis of the capsule chamber 1, simultaneously deflect clockwise or counter-clockwise, in order to provide a spiral airflow that flows upward from the deflected intake ducts 13 when the user inhales.

Compared with the foregoing embodiment, the inhaler of this embodiment is provided with a deflected intake duct group on the side wall of the capsule chamber 1 to provide a spiral airflow that moves upward from the deflected intake duct 13 when the user inhales. The airflow can help the capsules rotate and vibrate more smoothly to release the inhalable powder, which greatly reduces the requirement of the user's inhalation flow when the capsules rotate and release medicine, and can release the powder easier.

Further preferably, by referring to FIG. 13 and FIG. 14, in one embodiment, the deflected intake duct group is provided at the lower part of the side wall of each capsule chamber 1.

Compared with the previous embodiment, the inhaler of this embodiment provides a deflected intake duct group at the lower part of the capsule chamber 1, which can not only provide a spiral airflow moving upward from the deflected intake duct 13, but also assist the bottom of the intake duct 14 to make the top of the capsule rotate against the screen 12 at the top of the capsule chambers.

Further preferably, by referring to FIG. 17, in one embodiment, the direction of the deflected intake ducts 13 is tangent to the side wall of each capsule chamber 1, so that the spiral airflow can smoothly drive the capsules to rotate.

Figure 20:
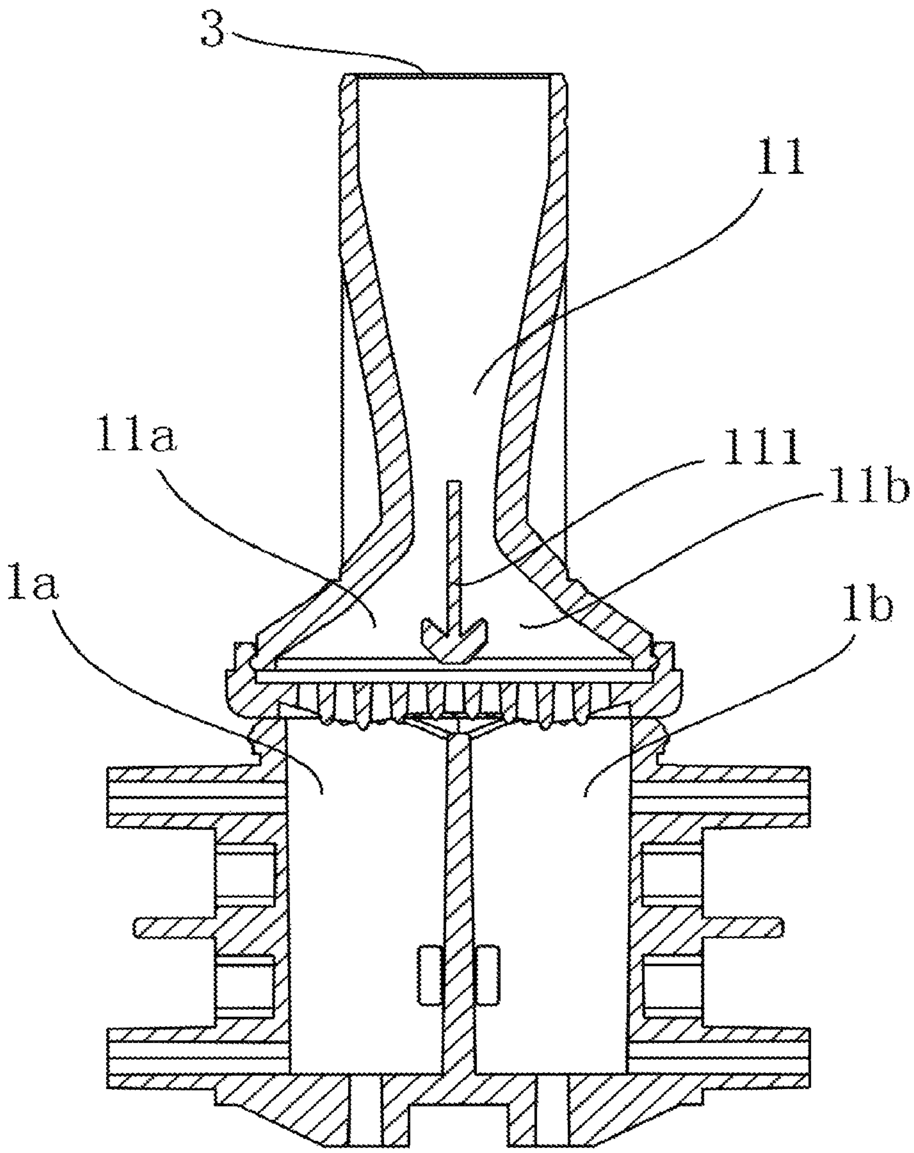
FIG. 20 is a partial sectional view of another dry powder inhaler of the present invention.

Further preferably, by referring to FIG. 20, in one embodiment, the lower part of the outlet duct 11 is divided by a central baffle 111 to form a first sub-duct 11*a* and a second sub-duct 11*b*, which are respectively connected to the tops of the first capsule chamber and the second capsule chamber, the first sub-duct 11*a* and the second sub-duct 11*b* gradually gather from the bottom to top toward the central baffle 111, the cross-sections thereof are gradually narrowed first and then remain unchanged, so that when the user inhales, the airflows in the first capsule chamber 1*a* and the second capsule chamber 1*b* are directed along the first sub-duct 11*a* and the second sub-duct 11*b* to merge in the upper part of the outlet duct 11 respectively.

Figure 21:
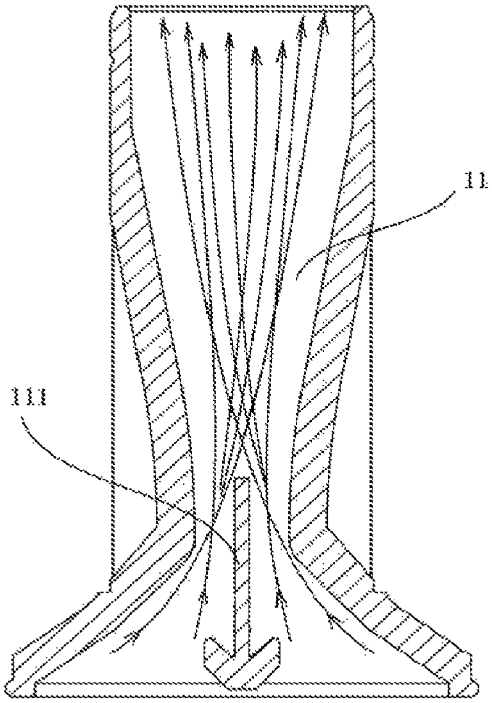
FIG. 21 is a sectional view of the airflow of the nozzle of the dry powder inhaler shown in FIG. 20.

By referring to FIG. 21, through the special design of the lower part of the outlet duct 11 of this embodiment, when the user inhales, the airflows in the two capsule chambers can be gathered in the area above the central baffle 111 and converged, and then be directed to flow above the outlet duct, so not only can the drug powder released in the two capsule chambers be fully mixed, but also can the collision with the duct be reduced, thereby the resistance when user inhales can be reduced.

More preferably, by referring to FIG. 20 and FIG. 21, in one embodiment, the cross-section of the outlet duct 11 gradually increases from the top of the central baffle 111 toward the nozzle 3 and then remains unchanged. when the user inhales, the airflows in the two capsule chambers(1*a*, 1*b*) can be gathered in the area above the central baffle 111 and converged, and then be directed to flow above the outlet duct, therefore, the cross-section of the outlet duct 11 of the present embodiment gradually increases from the top of the central baffle 111 toward the nozzle 3 and then remains unchanged, which is advantageous for air to flow upwards more smoothly, as the obstruction of the of the inner wall of the airflow duct 11 to the airflow is reduced and the collision of the drug powder in the airflow with the inner wall of the outlet duct 11 is reduced. It can be understood that, in order to achieve the above effect, the cross-section of the outlet duct 11 from the top of the central baffle 111 toward the nozzle 3 does not necessarily gradually increase and then remains unchanged, as long as it does not decrease.

Figure 22:
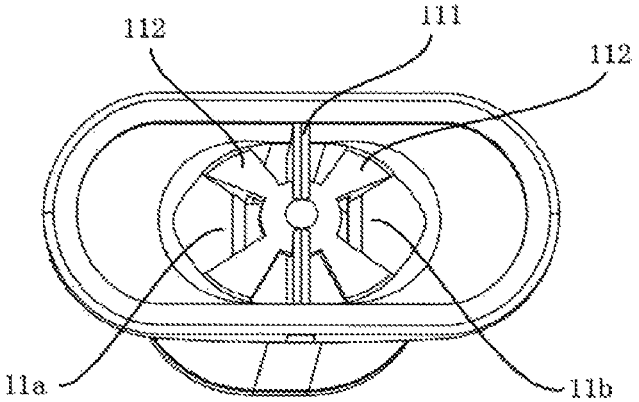
FIG. 22 is a plan view of the nozzle of the dry powder inhaler shown in FIG. 20.

More preferably, by referring to FIG. 22, in one embodiment, the first sub-duct 11*a* and the second sub-duct 11*b* further comprise two sub-baffles 112, and the first sub-duct 11*a* and the second sub-duct 11*b* are further divided by the sub-baffles 112 into a plurality of narrow ducts that gradually gather from the top of each capsule chamber from bottom to top toward the central baffle 111 respectively, the height of the sub-baffle 112 is lower than that of the central baffle 111. The cross-section of the sub-baffles is X-shaped, which is mirror-symmetrical with the central baffle 111 as the symmetry plane.

In this embodiment, the sub-ducts (11*a*, 11*b*) are further divided into six narrow ducts, each narrow duct can guide the direction of the gathered airflow more precisely according to its position, so as to make the airflows from the two capsule chambers (1*a*, 1*b*) gather more smoothly and converge on the upper area of the central baffle 111, and then be directed to flow above the outlet duct.

More preferably, by referring to FIG. 20, in one embodiment, the airflows from the first capsule chamber 1*a* and the second capsule chamber 1*b* flows along the first sub-channel 11*a* and the second sub-channel 11*b* to the upper part of the outlet duct 11 respectively when the user inhales, and the nozzle 3 is provided at a position where the airflows are sufficiently converged, and the height of the outlet duct 11 is 31 mm.

The height of the outlet duct 11 in this embodiment refers to the distance from the top of the capsule chamber to the nozzle 3, as shown in FIG. 21, in the vicinity of the nozzle at the end of the outlet duct, the airflow in the two capsule chambers (1*a*, 1*b*) has been fully converged, and the drug powder in the airflow is also fully mixed. Further increasing the distance of the outlet duct will increase the inhalation resistance.

Figure 15:
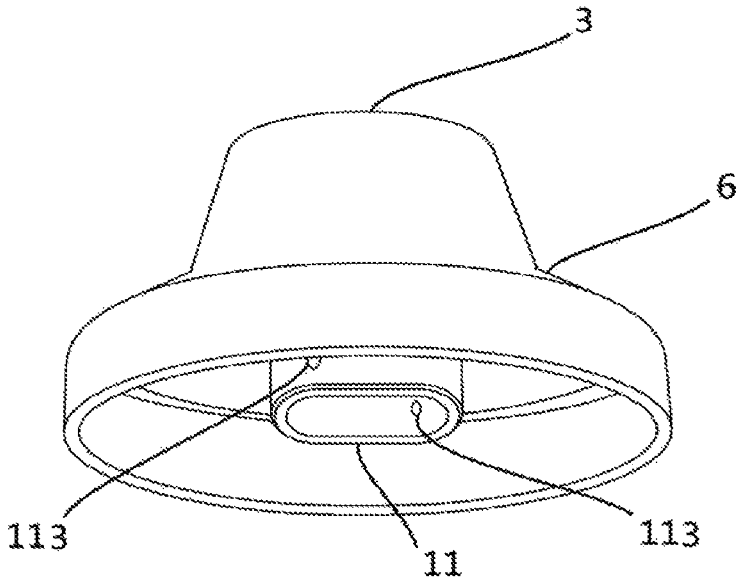
FIG. 15 is a perspective view of the nozzle of the dry powder inhaler shown in FIG. 13.
Figure 16:
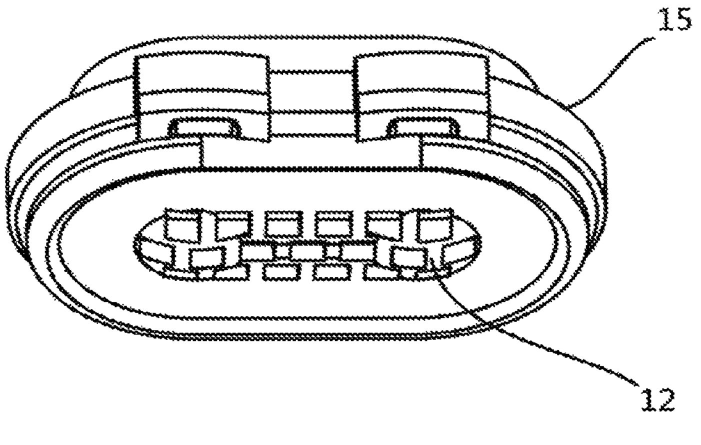
FIG. 16 is a perspective view of the screen cover of the dry powder inhaler shown in FIG. 13.

Further preferably, by referring to FIG. 13, FIG. 14 and FIG. 15, in one embodiment, the dry powder inhaler further comprises:

(d) the lower casing 4, which defines a cavity, the tope of which is open and is used for accommodating the double-capsule chamber, and the lower casing 4 is provided with two gaps 41 on the side thereof, so that at least one part of the each actuator 2 is provided located outside of the dry powder inhaler for user to operate, the gaps 41 extend downward and widen with respect to the size of the actuators 2 to provide an air intake 42, so that the inside of the cavity can ventilate with the outside air through the air intake 42; (e) the adapter plate 5 which covers the top of the lower casing 4, and a hollow port 51 is provided at the top of the multi-capsule chamber, and a screen cover 15 is detachably mounted to the hollow port 51 so that the screen 12 covers the top of each capsule chamber 1;

(f) the upper casing 6, which extends downward from the top of the nozzle 3, defines a cavity that is open at the bottom and surrounds the outlet duct 11, and covers the adapter plate 5 when the screen cover 15 is mounted at the hollow port.

First, the user separates the lower casing 4 and the upper casing 6 so as to separate the screen cover 15 from the top of the double-capsule chamber, then fills each capsule chambers 1 with capsules containing two different active ingredients, and then closes the upper casing 6 and the lower casing 4 so that the screen 12 covers the top of the capsule chambers 1 again; then, the user operates parts of the actuators 2 located out of the casings to puncture the capsules in the capsule chambers 1, the actuators 2 are reset by the elastic components commonly used in the prior art; finally, the user closely fits the mouth to the nozzle 3 and inhales in force, the outside air enters the cavity through the air intake hole 42 of the lower casing 4, and enters the capsule chambers 1 from the intake ducts 14 at the bottom of the capsule chambers 1, so that the capsules vibrate and rotate against the screen 12 to release the powder. The released powder from the capsule enters the outlet duct 11 through the screen 12 and finally enters the human body.

Compared with the previous embodiment, the dry powder inhaler of this embodiment adds the upper casing 6, the lower casing 4 and the adapter plate 5 on the premise of supporting the technical solution of the previous embodiment, thereby increasing the structural firmness of the dry powder inhaler, and making it easy to operate. The upper casing 6, the lower casing 4 and the adapter plate 5 are all conventional components of the same type of dry powder inhaler in the prior art. In this embodiment, the upper casing 6, the lower casing 4 and the adapter plate 5 are also conventional designs in the prior art.

Further preferably, by referring to FIG. 13, FIG. 14 and FIG. 15, in one embodiment, a slit 52 is provided at the junction of the upper casing 6 and the adapter plate 5, so that the internal cavity can ventilate with the outside air through the slit 52. The side wall of the outlet duct 11 is provided with a small hole 113, which is opened in a direction not facing the central axis of the outlet duct 11 to promote airflow rotate in the outlet duct 11 when the user inhales.

When the user inhales, external air can enter the internal cavity of the upper casing 6 through the slit and enter the outlet duct 11 from the small hole 113 of the outlet duct 11 to promote the rotation of the airflow in the outlet duct 11, in this embodiment, after the capsule medicine powder in each capsule chamber 1 is released, it is transmitted in the outlet duct 11 and fully mixed by rotation, so that the moving speed of the airflow arriving at the nozzle 3 is proper and the ingredients are uniform.

Further preferably, by referring to FIG. 14, in one embodiment, the diameter of the outlet duct 11 gradually decreases from bottom to top, and a narrow neck 114 is formed before reaching the outlet, so that the moving speed of the airflow arriving at the nozzle 3 is proper and the ingredients are uniform.

Figure 18:
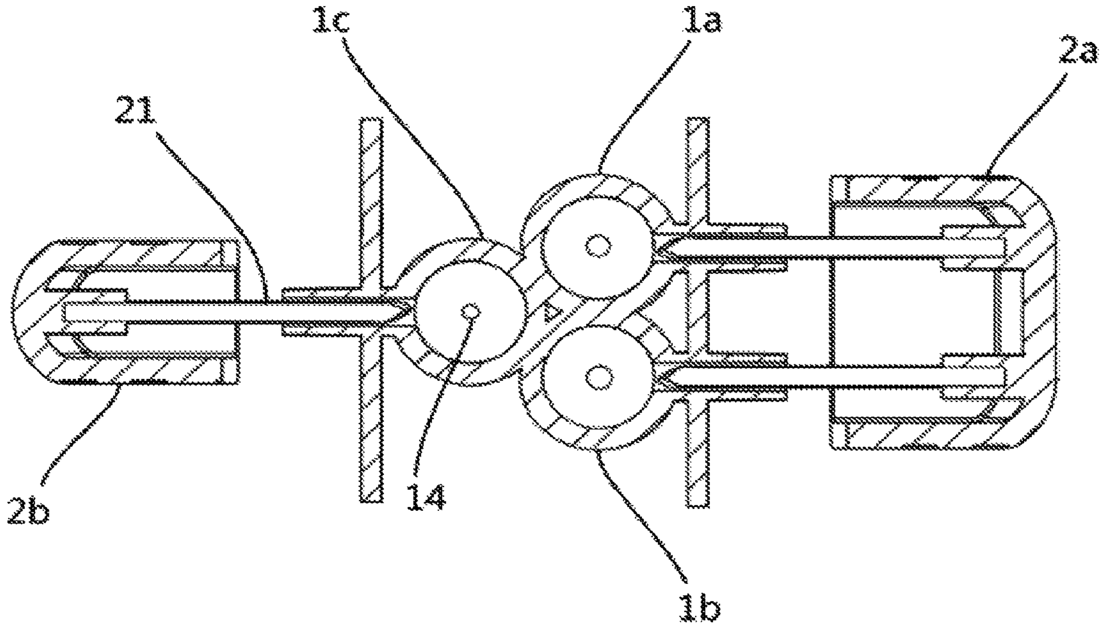
FIG. 18 shows a sectional top view of a multi-capsule chamber of another dry powder inhaler of the present invention.

By referring to FIG. 18, it is another embodiment of the dry powder inhaler of the present invention. The multi-capsule chamber is composed of a first capsule chamber 1*a*, a second capsule chamber 1*b*, and a third capsule chamber 1*c*, which are closely arranged into a triangle. The first actuator 2*a* is arranged on one side of a line where the first capsule chamber 1*a* and the second capsule chamber 1*b* are connected, and the first actuator 2*a* is provided with two needles 21 in the width direction, and the two needles can move to the multi-capsule chamber to puncture the capsules in the first capsule chamber 1*a* and the second capsule chamber 1*b* at the same time, and the second actuator 2*b* is arranged on a side of the third capsule chamber 1*c* away from the first capsule chamber 1*a* and the second capsule chamber 1*b*, and is movable in a direction perpendicular to the straight line where the first capsule chamber 1*a* and the second capsule chamber 1*b* lie to puncture the capsule in the third capsule chamber 1*c*.

This embodiment provides a medicine dispenser containing three active components (or a mixture thereof) in a separated manner by providing three capsule chambers, and an intake duct 14 is provided at the bottom of each capsule chamber 1, and no deflected intake duct group is provided on the side or bottom of each capsule chamber. The arrangement of other components is the same as or similar to that in other embodiments, and details are not described herein again.

Further preferably, by referring to FIG. 18, in one embodiment, the diameter of the bottom intake duct 14 of one capsule chamber 1 is different from that of the other two capsule chambers, so that the intake airflow rate of the capsule chamber is different from that of the other capsule chambers.

In some cases, each component of the combined product needs to achieve a specific particle distribution to maximize its effect. Since each component of the present invention is released separately in each corresponding capsule chamber 1, by adjusting structural characteristics such as the size, position, opening angle, and/or the number of the intake ducts 13, the intake ducts 14, and/or the air outlet duct 11, different aerodynamic parameters can be set for each capsule chamber 1, in order to maximize the therapeutic effect of each active ingredient under the premise of simultaneous administration. In this embodiment, the size of the intake duct 14 at the bottom of the capsule chambers 1 is adjusted to give different air flow rates to affect the particle distribution of the powder in the capsules.

Figure 19:
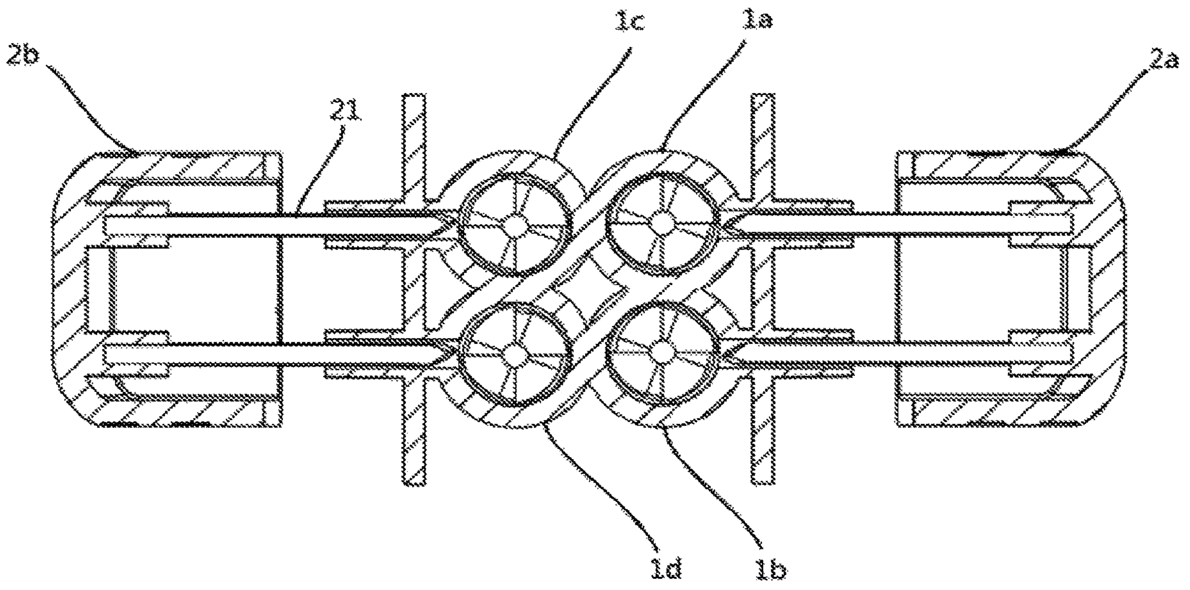
FIG. 19 shows a sectional top view of a multi-capsule chamber of another dry powder inhaler of the present invention.

By referring to FIG. 19, it is another embodiment of the dry powder inhaler of the present invention, the multi-capsule chamber 1 is composed of the first capsule chamber 1*a*, the second capsule chamber 1*b*, the third capsule chamber 1*c* and the fourth capsule chamber 1*d*, which are arranged closely as a square. The first actuator 2*a* and the second actuator 2*b* are arranged on the central axis of the square and can move from both sides to the middle, the first actuator 2*a* and the second actuator 2*b* comprises at least two needles 21 in the width direction so that the first actuator 2*a* simultaneously punctures the capsules in the first capsule chamber 1*a* and the second capsule chamber 1*b*, and the second actuator 2*b* simultaneously punctures the capsules in the third capsule chamber 1*c* and the fourth capsule chamber 1*d*.

This embodiment provides a medicine dispenser containing four active components (or a mixture thereof) in a separated manner by providing four capsule chambers. Providing four capsule chambers results in a higher requirement for the inhaler for the patient's inspiratory flow. In order to rotate and vibrate the capsule fully to release the inhalable powder, each capsule chamber 1 of this embodiment is provided with a deflected intake duct group at the bottom of the capsule chamber, and the intake duct group is arranged as a fixed impeller to provide a spiral air flow from bottom to top when the user inhales, which effectively promotes the capsule's rotation and vibration to release the inhalable powder. The specific shape of the impeller structure is shown in FIG. 10.

The above are only the specific embodiments of the present invention and are not intended to limit the scope of the present invention. Any equivalent change, modification and combination made by persons skilled in the art without departing from the concept and principle of the present invention shall fall within the protection of this application.

What is claimed is:

1. Dry powder inhaler, comprising:

capsule chambers (1), which are cylindrical chambers for holding capsules upright, tops of the capsule chambers (1) are open, and bottoms of the capsule chambers (1) are provided with intake ducts ventilating with outside air;

actuators (2), comprising puncture needles (21), mounted for a user to operate to move toward a side wall of each of the capsule chambers (1) to puncture the capsules;

nozzle (3), comprising an outlet duct (11) under the nozzle (3);

wherein, a number of the capsule chambers (1) is two, and all the capsule chambers (1) are arranged in parallel to form an integral multi-capsule chamber, the actuators (2) are mounted individually or in common among the capsule chambers (1), and the actuators (2) are mounted with needles (21) in a width direction of the actuators (2), a screen cover (15) is mounted at a bottom of the outlet duct (11) under the nozzle (3), and a screen (12) is fixed in the screen cover (15) and separately connected to the top of the multi-capsule chamber, making the screen (12) cover the tops of all of the capsule chambers (1), wherein each capsule chamber (1) is provided at the side wall of the capsule chamber (1) with at least one deflected intake duct group, the deflected intake duct group comprises at least two deflected intake ducts (13) which are arranged around a central axis of the capsule chamber (1), and simultaneously deflect clockwise or counterclockwise, wherein a lower part of the outlet duct (11) is divided by a central baffle (111) to form two sub-ducts, which are respectively connected to the top of each capsule chamber (1), each cross-section of each respective sub-duct gradually narrowing from the tops of the capsule chambers towards an upper part of the outlet duct, wherein each cross-section stops narrowing and then remains a same size until the sub-ducts converge together into one duct at the upper part of the outlet duct, wherein the central baffle extends from the tops of the capsule chambers towards the nozzle at least to a point where the sub-ducts stop narrowing, wherein each sub-duct comprises one or more sub-baffles, the sub-baffles divide the sub-duct into narrower ducts, wherein the narrower ducts converge into a respective sub-duct above the sub-baffles.

2. The dry powder inhaler of claim 1, wherein the at least two deflected intake ducts (13) of the deflected intake duct group of each capsule chamber (1) have a same shape and size, and are evenly arranged around the central axis of the capsule chamber (1).

3. The dry powder inhaler of claim 2, wherein the at least two deflected intake ducts (13) of each capsule chamber (1) are tangent to the side wall of their respective capsule chambers (1).

4. The dry powder inhaler of claim 1, wherein an opening of each of the at least two deflected intake ducts (13) on the side wall of each capsule chamber (1) has a long-strip shape, which is arranged longitudinally along the side wall.

5. The dry powder inhaler of claim 1, wherein a size of the intake duct and/or top opening of at least one of the capsule chambers (1) is different from others of the capsule chambers (1).

6. The dry powder inhaler of claim 1, wherein the cross-section of the outlet duct (11) gradually increases in a direction from a top of the central baffle (111) toward the nozzle (3).

7. The dry powder inhaler of claim 6, wherein the cross-section of the outlet duct (11) gradually increases, and then remains the same size.

8. The dry powder inhaler of claim 1, wherein a height of the sub-baffles (112) is lower than a height of the central baffle (111).

9. The dry powder inhaler of claim 1, wherein the cross-section of each sub-baffle (112) is arranged radially with the center baffle (111) as a center.

10. The dry powder inhaler of claim 9, wherein a shape of the cross-section of each sub-baffle (112) is X-shaped, which takes the central baffle (111) as a plane mirror symmetry.

11. The dry powder inhaler of claim 10, wherein an air resistance of the dry powder inhaler is 0.0325 $KPa^{0.5}$ minutes/liter.

12. The dry powder inhaler of claim 10, wherein a length of the outlet duct (11) is 25-36 mm.

13. The dry powder inhaler of claim 1, wherein the multi-capsule chamber is composed of a first capsule chamber (1*a*) and a second capsule chamber (1*b*) which are closely arranged, and the actuators (2) comprise a first actuator (2*a*) and a second actuator (2*b*), which are arranged at both ends of a connecting line where the first capsule chamber (1*a*) and the second capsule chamber (1*b*) are located, the first actuator (2*a*) is movable from both sides of the first capsule chamber (1*a*) to a middle of the first capsule chamber (1*a*), and the second actuator (2*b*) is movable from both sides of the second capsule chamber (1*b*) to a middle of the second capsule chamber (1*b*), so as to puncture the capsules in the first capsule chamber (1*a*) and the second capsule chamber (1*b*), respectively.

14. The dry powder inhaler of claim 1, further comprising a lower casing, which defines a cavity, the top of which is open and is used for accommodating the multi-capsule chamber inside, the side of the lower casing is provided with gaps that match a number and positions of the actuators, so that part of each actuator is located outside the dry powder inhaler, and the cavity ventilates with outside air.

15. The dry powder inhaler of claim 14, further comprising an adapter plate, which covers the top of the lower casing, and a hollow port is provided at the top of the multi-capsule chamber, the screen cover is detachably mounted to the hollow port so that the screen covers the top of each capsule chamber through the hollow port.

16. The dry powder inhaler of claim 15, further comprising an upper casing, which extends downward from a top of the nozzle, defines a cavity surrounding the outlet duct and the bottom of the cavity being open, and covers the adapter plate when the screen cover is mounted at the hollow port.

* * * * *